United States Patent

Chevillon et al.

Patent Number: 5,853,420
Date of Patent: Dec. 29, 1998

[54] ASSEMBLY COMPRISING A BLOOD FILTER FOR TEMPORARY OR DEFINITIVE USE AND DEVICE FOR IMPLANTING IT, CORRESPONDING FILTER AND METHOD OF IMPLANTING SUCH A FILTER

[75] Inventors: Gérard Chevillon, Montrouge; Guy Nadal, Poitiers, both of France; Massimo Iachetti, Rome, Italy

[73] Assignee: B. Braun Celsa, Chasseneuil Du Poitu, France

[21] Appl. No.: 811,294

[22] Filed: Mar. 4, 1997

Related U.S. Application Data

[63] Continuation-in-part of Ser. No. 424,086, Apr. 19, 1995, Pat. No. 5,634,942.

[30] Foreign Application Priority Data

Apr. 21, 1994 [FR] France ................... 94 04804
Apr. 14, 1995 [EP] European Pat. Off. ......... 95 400 850.4

[51] Int. Cl.$^6$ ........................................ A61F 2/01
[52] U.S. Cl. ................................ 606/200; 606/194
[58] Field of Search .................. 623/1, 12; 606/191, 606/194, 195, 198, 200

[56] References Cited

U.S. PATENT DOCUMENTS

| | | |
|---|---|---|
| 4,425,908 | 1/1984 | Simon . |
| 4,990,156 | 2/1991 | Lefebvre .................. 606/200 |
| 5,059,205 | 10/1991 | El-Nounou et al. ........ 606/200 |
| 5,108,418 | 4/1992 | Lefebvre .................. 606/200 |
| 5,234,458 | 8/1993 | Metals .................... 606/200 |
| 5,300,086 | 4/1994 | Gory et al. ............... 606/200 |
| 5,344,427 | 9/1994 | Cottenceau et al. ........ 606/200 |
| 5,350,398 | 9/1994 | Pavcnik et al. ........... 606/200 |
| 5,370,657 | 12/1994 | Irie ...................... 606/200 |
| 5,375,612 | 12/1994 | Cottenceau et al. ........ 606/200 |
| 5,383,887 | 1/1995 | Nodal .................... 606/200 |

FOREIGN PATENT DOCUMENTS

| | | |
|---|---|---|
| 2587901 | 4/1987 | France . |
| 2649884 | 1/1991 | France . |

Primary Examiner—Paul B. Prebilic
Assistant Examiner—Bruce E. Snow
Attorney, Agent, or Firm—Pollock, Vande Sande & Amernick

[57] ABSTRACT

The invention relates to an assembly using a vascular filter accommodated in an implanting sleeve from which it can be partially expelled in the case of temporary filtration. It is used by means of a maneuvering rod to which the filter is connected in a separable manner so that the filter is separated therefrom, and then expelled into the sleeve. The filter may have legs in the shape of a corolla and extensions for retaining it in place in the blood vessel, which naturally define a cylinder. Its use is for the treatment of risk of embolism.

6 Claims, 4 Drawing Sheets

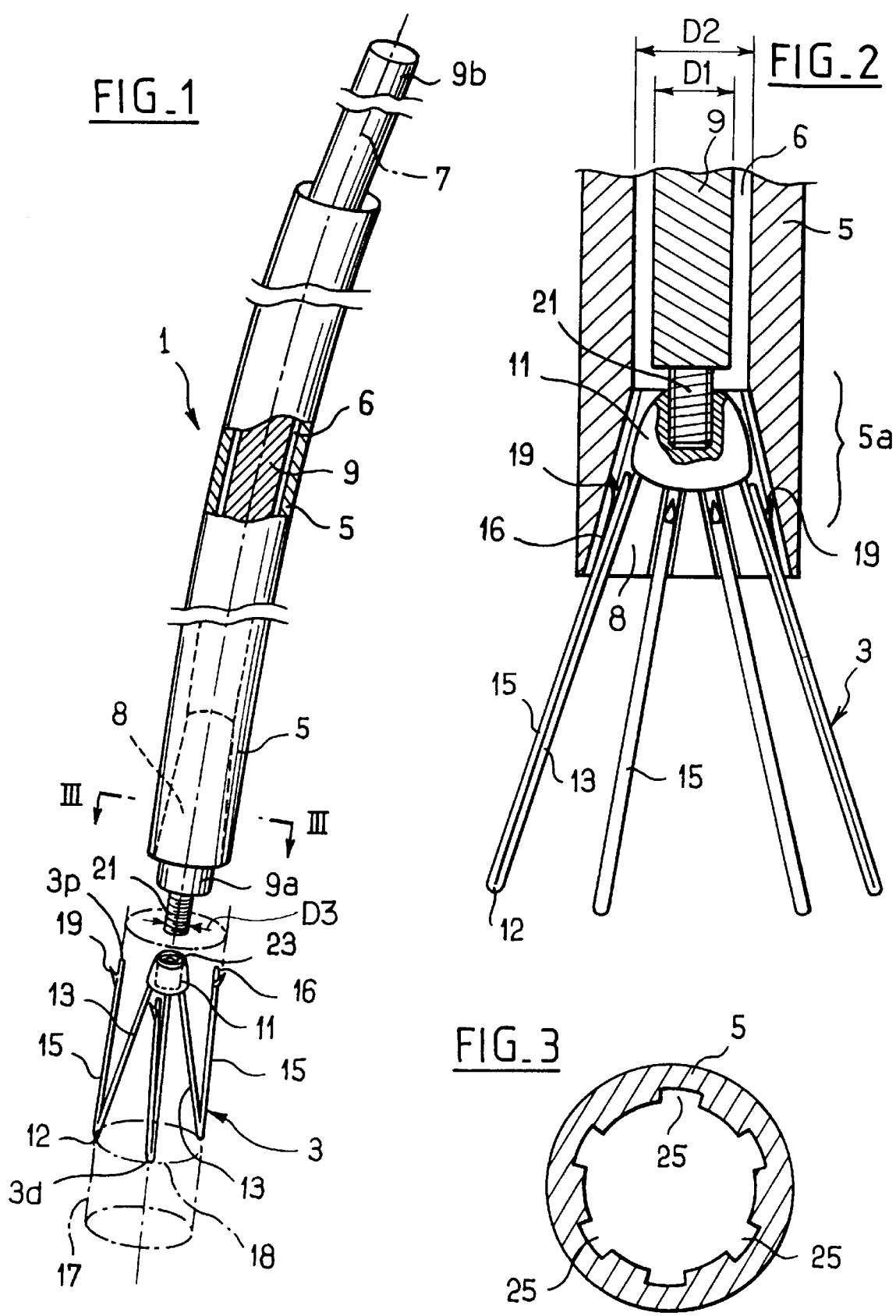

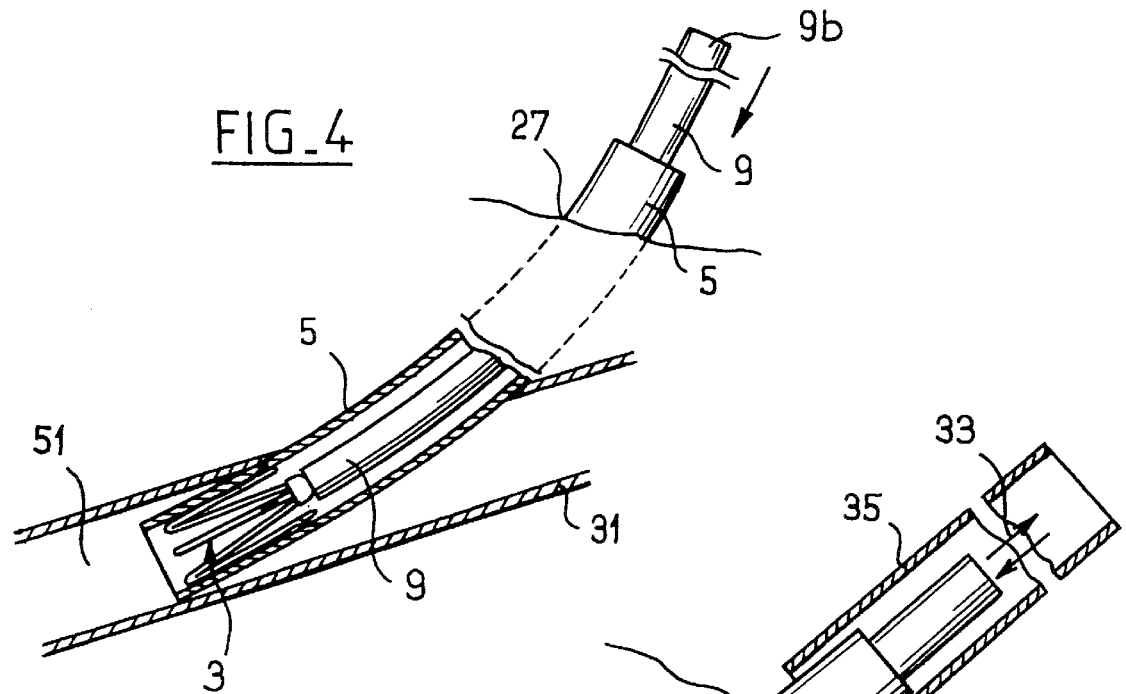
FIG_4
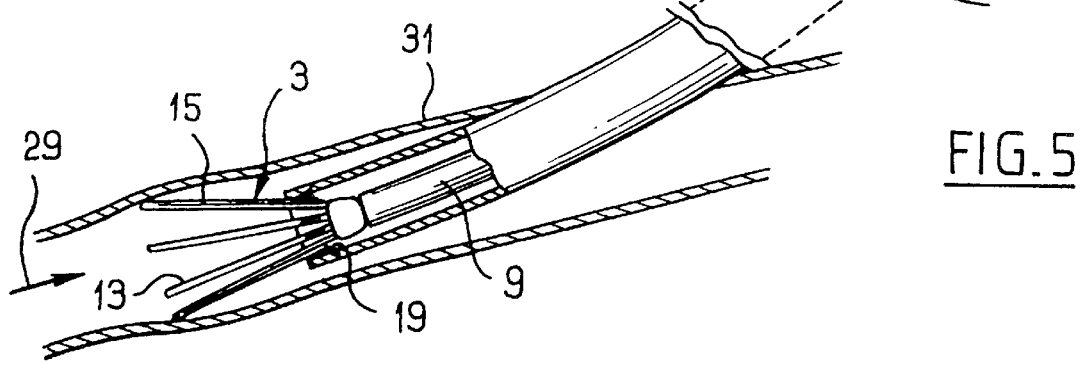
FIG_5
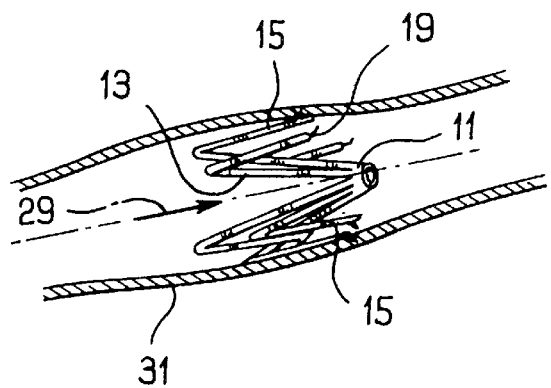
FIG_6

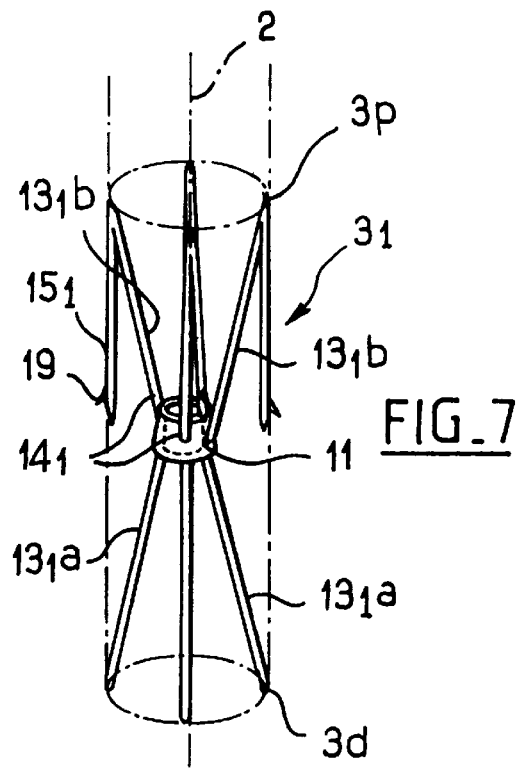
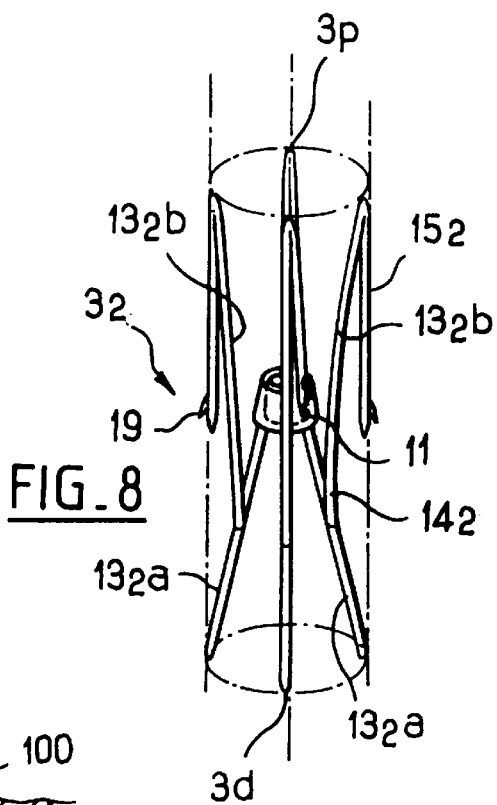
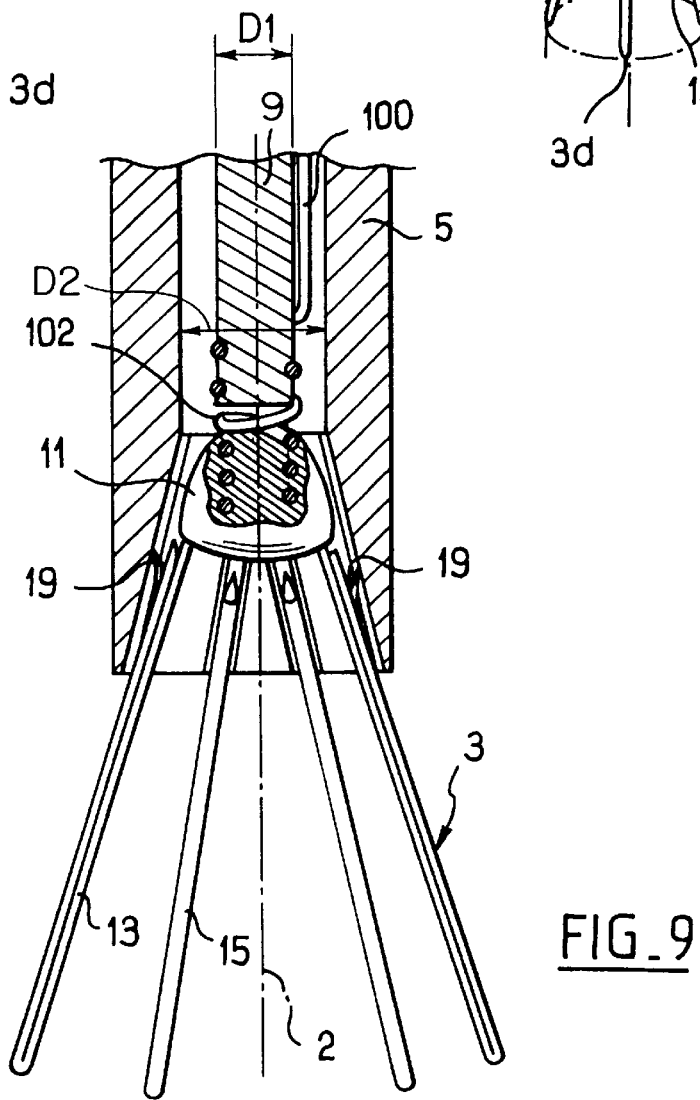

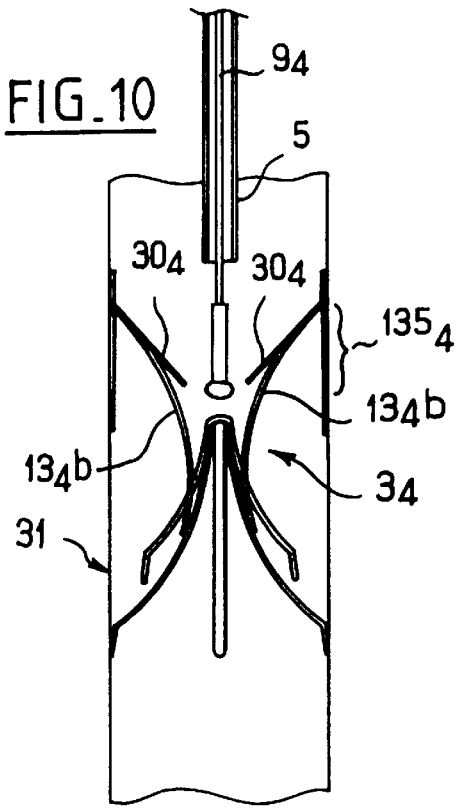
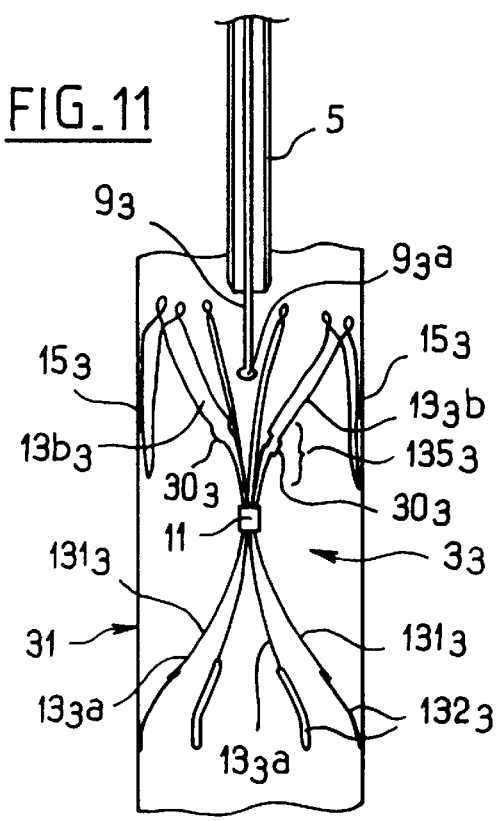
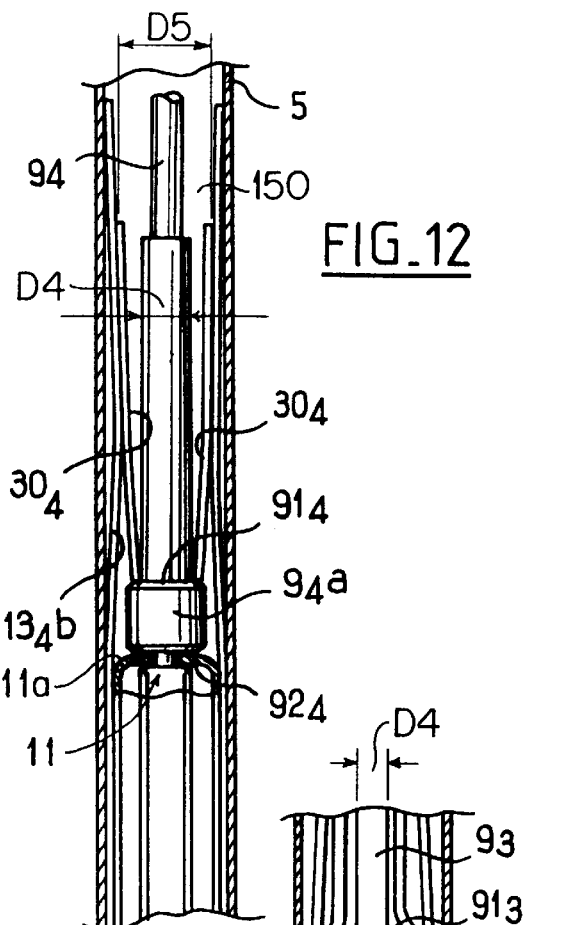
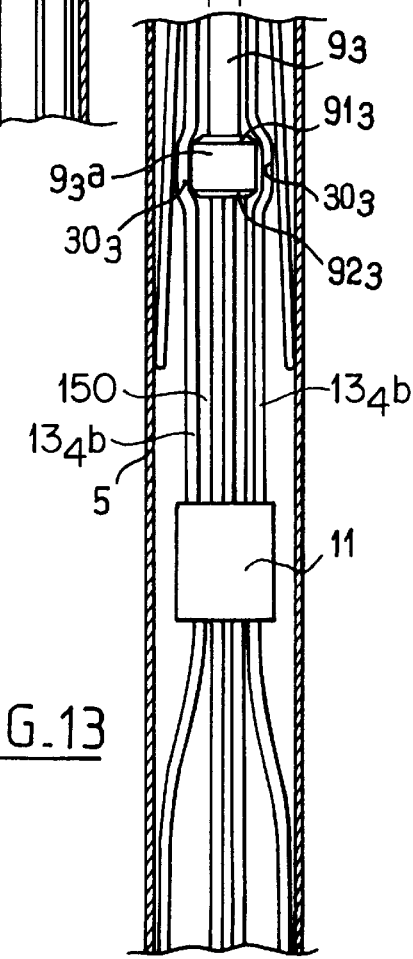

5,853,420

ASSEMBLY COMPRISING A BLOOD FILTER FOR TEMPORARY OR DEFINITIVE USE AND DEVICE FOR IMPLANTING IT, CORRESPONDING FILTER AND METHOD OF IMPLANTING SUCH A FILTER

This application is a continuation-in-part of U.S. patent application Ser. No. 08/424,086, filed Apr. 19, 1995, now U.S. Pat. No. 5,634,942.

FIELD OF THE INVENTION

The invention relates to a medical filter adapted to be positioned in a blood vessel in order to trap any clots that may be circulating there.

The invention relates also to an assembly comprising such a filter and its implanting device.

BACKGROUND OF THE INVENTION

In order to implant these filters in the body of a patient, the practitioner generally uses the intravenous route, either exposing the vessel or using an introduction technique referred to as the percutaneous technique.

The percutaneous technique is the less aggressive because a device of the type used for introducing a catheter can be used in order to introduce the filter via the jugular or femoral vein. When an incision has been made in the skin, the filter is introduced into the vein concerned and is then guided as far as the inferior vena cava where it is "expelled" from the device. It expands in the vein, thereby preventing the migration of clots moving towards the heart and the pulmonary artery, and avoiding embolism.

Depending on the risks involved, two major categories of filters are available today.

First of all, in the face of a serious risk of embolism, filters referred to as "definitive" filters are proposed, that is to say, filters intended for permanent implantation.

Such filters are described, for example, in patents U.S. Pat. No. 3,540,431, U.S. Pat. No. 4,688,553 or in FR-A-2 689 388.

In those two typical cases, the filter is made up of filiform elements (round filaments or the like) arranged so as to define a corolla, the axis of which must advantageously be orientated substantially along the axis of the vessel, in order to obtain the best clot-retaining effect, without disturbing to an excessive extent the circulation of blood in respect of which the filter is permeable.

Having been implanted definitively, those filters have to be secured to the vein and, to that end, they often comprise hooks which anchor themselves in the wall of the vessel at the moment when the filter is released and expands radially (often by itself, a number of filters being "self-expansible").

At present, the implanting device for those filters comprises a sleeve which extends from outside the patient's body and in which the filter is retained in the radially restrained state, and a maneuvering rod which is mounted to slide in the sleeve and which permits, at the appropriate moment, the expulsion of the filter out of that sleeve, which is then withdrawn with the rod.

In some cases, however, the risk of pulmonary embolism does not necessitate permanent in situ filtration treatment. In that case, filters referred to as "temporary" filters have already been proposed (for example described in FR-A-2 694 687 or FR-A-2 657 261), that is to say, filters having a structure such that they can be withdrawn after having been implanted.

Usually, they are medical instruments having an external sleeve in which slides a maneuvering rod, at one end of which a filtering means is secured in a definitive manner and may, in particular, again be in the form of a filiform structure developing naturally in the shape of a conical corolla which is radially restrained in the sleeve as long as the filter is not in operation, the releasing of the filter still being effected by relative axial displacement of the sleeve and the rod, which enables the filtration corolla to open out. Insofar as the filtering means do not have an anchoring hook and are held by the rod, they can be withdrawn by the venous access route.

These temporary or definitive filters have the disadvantage of being selective, that is to say, if the practitioner first of all judges it necessary to use a temporary filter and then later judges that a definitive filter is required, it is absolutely necessary for him to withdraw the first and then implant the second. Conversely, if he has implanted a definitive filter straight away, it is too late to think of using a temporary filter.

In view of the, sometimes great, difficulty which the practitioner has in evaluating straight away the degree of risk of embolism, EP-A-0 348 295 has proposed a filtration assembly for temporary and/or definitive use which comprises, on the one hand, a filter having flexible legs defining two head-to-tail corollas (one for filtration and one for retaining the filter definitively implanted in the vessel) and, on the other hand, a double catheter for retaining the filter in temporary implantation. The double catheter comprises an external catheter which, when the assembly is used temporarily, contains the filter-retaining corolla which is then in a radially restrained state (the filtration corolla being expanded in the vessel) and an internal catheter which is mounted to slide in the external catheter for the complete expulsion of the filter from the external catheter (on passing from temporary use to definitive use of the filter). In the case of temporary use, the filter is retained connected to the double catheter simply by the friction of the legs of its retaining corolla against the wall of the external catheter.

In the case of definitive use, the filter is completely expanded in the vessel, with its retaining corolla supported against the wall of the vessel in order to secure the filter there, the double catheter normally being withdrawn from the patient's body.

In order to position the assembly, an implanting apparatus is used which comprises an implanting sleeve through which the double catheter carrying the filter is made to slide, the double catheter forming a pusher for the filter in order to direct it through the sleeve as far as the implantation area.

In practice, this assembly has not always proved to be completely reliable and has been found to be complicated and tricky to manipulate for the implantation of the filter. It has been noted in particular that:

three coaxial tubes (sleeve and double catheter) are necessary for the correct implantation of the filter, which increases the bulk (cross-section) of the system and complicates its introduction into sinuous or narrow channels;

any accidental movement of the internal catheter relative to the external catheter would cause undesirable displacement of the filter inside the external catheter (which could weaken the support of the filter) and even an expulsion of the filter from the sleeve;

the internal catheter acts on the filter at the proximal end of the latter and apart from the head, which does not always make its displacement easy;

in addition, the internal catheter displaces the filter only in the direction of its expulsion from the external catheter, which does not always permit a control of the displacement of the filter, especially for satisfactory positioning in the vessel.

In order to control somewhat the ejection of a definitive filter from its implanting sleeve, it has already been proposed, in FR-A-26 45 028, to equip a conventional system for the implantation of definitive filters with means for the releasable connection of the pusher-rod to the proximal end of the filter, that rod then having a recessed distal end for receiving the head of the filter and gripping it for as long as it is tightly arranged inside the sleeve.

To the applicant's knowledge, there has never yet been proposed an assembly for temporary and/or definitive filtration which has a simple structure, is reliable and comprises releasable connection means provided on the pusher-rod and on the filter. Even if it had been decided to use the relatively simple system provided with releasable connection means of FR-A-26 45 028 for implanting the filter for temporary and/or definitive use of EP-A-0 348 295, the mounting solution naturally adopted, bearing in mind the teaching of those documents, would have been to clamp the proximal end of the legs of the corolla for retaining the filter in the recessed distal end of the rod, such a method of mounting not really providing any solution to the problems of control and facility of displacement of the filter by the pusher-stem.

BRIEF DESCRIPTION OF THE INVENTION

In view of the above and in order to harmonize the advantages of temporary filters and definitive filters, the invention proposes a solution which permits the transition of the filter, once implanted, from a temporary use to a definitive use, without the requirement for a long and delicate operation and without changing instruments, under conditions of reliable implantation and easy control of the displacements of the filter in the body.

In this connection, it should be noted that the invention is also very especially concerned with rendering such a "multi-use" filter reliable, ensuring, in particular, that, if it is used within the framework of temporary implantation, it can be withdrawn quite safely, the filter also being designed to provide the practitioner with every opportunity to position it so that it is centred in the vessel, at the same time ensuring that it has a high degree of stability.

It is therefore in order to fulfil those requirements that the invention first of all proposes a vascular filter adapted to expand radially with respect to the axis of the vessel, the filter having a proximal end, an opposing distal end and comprising:

filtering means which comprise first legs projecting from a head and arranged to extend from that head towards the distal end of the filter, substantially in the shape of a first corolla in a radially unrestrained state;
  means for retaining in place relative to the vessel, which are connected to the filtering means and comprise securing means arranged at a distance from the distal end of the filter, those retaining means defining, in a radially unrestrained state, a substantially cylindrical axial tubular surface so that the securing means are in contact with a wall of the vessel in order to keep the filter secured there when the latter is positioned there; and
  releasable connection means for a separable connection of the filter to a maneuvering rod of the device for implanting the filter, a part of the releasable connection means being carried by the retaining means, in an area of the latter means intermediate between the proximal and distal ends of the filter, or by the head, the connection permitting axial displacement of the filter in opposing directions in relation to the implanting sleeve in which the rod is slidably mounted, in such a manner that:
    in the case of temporary filtration use, the filter is partially located in an end portion of the sleeve, with its retaining means radially restrained and its securing means contained inside the sleeve, while its filtering means are at least partially radially expanded in the vessel; and
    in the case of definitive filtration use, the filter is completely outside the sleeve and separated from the rod, with its retaining means radially expanded, in accordance with the substantially cylindrical tubular surface.

In order to ensure maximum efficacy in terms of reliability of filtration, of limitation of the risks of damage to the vessel and of non-migration of the filter once implanted, another feature of the invention provides that, advantageously:

the retaining means comprise second legs, at least some of which are lengthened by extensions, each leg and its extension then being in the general form of a hairpin, the second legs being secured, towards one of their ends, to the filtering means in such a manner that, in an unrestrained state of the retaining means:
  the second legs extend from the end at which they are secured to the filtering means in the direction towards the proximal end of the filter, substantially in the shape of a second corolla, the two corollas being arranged head-to-tail; and
  the extensions run, over at least a portion of their length, in the direction towards the first corolla, substantially parallel to the axis of the filter, in so doing defining the said tubular surface, and are supported against the wall of the vessel when the filter is positioned there.

With regard to the medical assembly using the filter proposed by the invention, it preferably comprises, in addition to the filter, a device for implanting the filter comprising:

an implanting sleeve in which the filter is arranged in a radially folded state for its implantation, the sleeve having a proximal end and a distal end;
  a rod which can be maneuvered from the proximal end of the sleeve in which it is slidably mounted, in order to manoeuvre the filter by pushing it, at least partially, out of the distal end of the sleeve; and
  the maneuvering rod comprises a part of the releasable connection means (arranged towards its distal end) cooperating with the remainder of those means carried by the filter so that they can be connected to one another in a separable manner, permitting axial displacement of the filter in two opposing directions in relation to the sleeve in the case of temporary use of the filter.

Also in order to simplify the assembly of the invention, the rod advantageously comprises a single cylindrical elongated element.

The rod/filter connection can be affected by screwing, in which case the sleeve advantageously comprises, towards its internal distal end, anti-rotation notches adapted to cooperate with the filter in order to prevent it from rotating when it is decided to pass from temporary use to definitive use.

Other features and advantages of the invention will also become apparent in the following description given with reference to the attached drawings, in which:

BRIEF DESCRIPTION OF THE FIGURES

FIG. 1 is a general diagrammatic view of the main features of the means of the invention, with a local cut-away portion;

FIG. 2 is a diagrammatic longitudinal section through a filter in the case of temporary use;

FIG. 3 is a sectional view along the line III—III of FIG. 1;

FIGS. 4, 5 and 6 show three successive phases of use of the means of the invention within the framework of a temporary use (FIG. 5) and then a definitive use of the filter (FIG. 6);

FIGS. 7 and 8 show two variants of the filter of FIG. 1;

FIG. 9 shows a variant of the connection of the rod to the filter of the assembly of FIG. 2;

FIGS. 10 and 11 show third and fourth variants, respectively, of the filter of the invention; and FIGS. 12 and 13 show, respectively, in an enlarged and partial view, the filters of FIGS. 10 and 11 arranged in the implanting sleeve, in a radially restrained state.

DETAILED DESCRIPTION OF THE INVENTION

Illustrated in FIG. 1 is an assembly according to the invention which comprises a device 1 for implanting and using a blood filter 3, the general features of the device 1 being known (for example described in FR-A-2 657 261 or U.S. Pat. No. 4,688,553).

To summarize, it essentially comprises an external sleeve 5 which is manufactured from biocompatible material and has a general longitudinal axis 7 and inside which the filter 3 may be accommodated in a radially folded state.

In order to act on the filter (which may be manufactured from a metal alloy), a maneuvering rod 9, manufactured from biocompatible material, is mounted to slide axially in the sleeve.

In a manner known per se (see, for example, the two publications mentioned above), the filter 3, which has an axis 2, a proximal end $3_p$ and an opposing distal end $3_d$, comprises a head 11, for example in the form of an ogive, from which project legs 13, at least some of which are lengthened at their free ends 12 by extensions 15 for centering and retaining the filter against the vessel. Those extensions run back, towards the head 11, in such a manner that the legs thus constituted are in the general form of a hairpin.

The legs and the extensions to which they are connected may be in the form of simple or looped metal wire, or in the form of fine blades, so that, in a radially unrestrained state, the filter 3 spreads out, in the area of the legs 13, into a substantially conical corolla, widening from the head 11 to the end $3^d$, while the extensions 15 run in the direction towards the closed end of the cone, being substantially parallel to the wall of the cylinder 17 generated by a generating line parallel to the axis 7 of the cone formed by the filter and generating the line 18 defining the opening perimeter of the filter.

Because the filter can be used for definitive implantation, it is equipped with securing or anchoring means 19. However, according to an important feature of the invention, the hooks 19 have in this case been provided solely on the extensions 15, in the area of their free ends 16, so as to avoid any risk of undesired anchoring in the case of "temporary" use, as will be seen hereinafter.

Precisely with regard to such a non-definitive use, the distal end 9a (which is to be implanted the more deeply in the patient) of the flexible push rod or stem 9 and the head 11 of the filter are designed in such a manner that they can be releasably connected to one another.

In this case, the releasable connection means comprise mechanical means, for example, means for relative screwing.

For that purpose, the end 9a of the flexible rod having an external diameter D1 smaller than the internal diameter D2 of the sleeve has a threaded axial extension 21 adapted to engage in an internal screw thread 23 provided axially in the head 11 of the filter. The extension 21 has an external diameter D3 less than D1, as shown in FIGS. 1 and 2.

FIG. 2 shows, in addition to the filter 3 and the device 1 used together within the framework of a temporary implantation of the filter, the arrangement of the hooks 19 inside the sleeve 5, in connection with the partially retracted arrangement of the filter.

If, as in the present example, the rod/filter connection means comprise means for relative screwing, it has also been provided in the invention that the sleeve has a notched internal surface at its distal end portion marked by the area 5a. As shown in FIG. 3, a series of internal notches 25 in the form of slots substantially parallel to the axis 7 of the sleeve can be provided so that each slot receives one of the extensions 15 while acting on it in order to constitute anti-rotation means for the filter when the practitioner acts on the stem 9 in order to unscrew it with a view to passing from temporary implantation to definitive implantation. Preferably, the same number of notches 25 as extensions are provided, the natural outward radial resilience of the extensions promoting their engagement in the notches.

FIG. 2 also shows that the distal area 5a of the tubular sleeve can have an axial internal passage 8 having an enlarged diameter relative to that 6 located upstream, in order to promote good positioning of the head of the filter and an opening diameter sufficient for the opening out of the filter in the temporary implantation position.

Referring now to FIGS. 7 and 8, a first variant $3_1$ and a second variant $3_2$ of the filter of the invention are shown. They comprise, as the filter 3, a substantially conical filtration portion which does not have means for anchoring to the vessel and is formed by the head 11 (in this case provided with means of connection to the rod 9) from which project first legs $13_1a$, $13_2a$ which are substantially rectilinear and extend as far as the distal end $3_d$ of the filter.

The cooperation between filters $3_1$ (FIG. 7) and $3_2$ (FIG. 8) and the "pusher" corresponds to what is shown in FIG. 2. That is, an end of the flexible push rod or stem 9 and a cooperating profile head 11 can be mutually releasably engaged (cooperating thread) to complete a releasable connection between the filter and the push rod or stem 9.

Unlike the filter 3, the filters $3_1$ and $3_2$ each comprise a series of second legs $13_1b$ and $13_2b$, at least some of which are lengthened by extensions $15_1$ and $15_2$ for retaining in place and centering the filters $3_1$ and $3_2$, respectively, in the vessel. Those extensions comprise means 19 for securing the filter against the wall of the vessel, the hooks 19 being at a distance from the end $3^d$ of the filter. The second legs and their extensions are in the general form of a hairpin and can be produced from a single piece.

According to FIG. 7, the legs $13_1b$ of the filter $3_1$ are fixed at a securing end $14^1$ to the filtering portion (at the head 11). They extend from the head as far as the end $3_p$ of the filter in such a manner that, in their radially unrestrained state, they define a second substantially conical corolla, the first filtering corolla and the second corolla being head-to-tail.

According to FIG. 8, each leg $13_2b$ is secured to a leg $13_2a$ at a portion or area of that leg that is at a distance from its opposite ends (for example, substantially in its center) so that, in their unrestrained state, the legs $13_2b$ extend from the end $14_2$ at which they are secured to the legs $13_2a$ in the shape of a second corolla or a flared tubular surface having an axis 2 (which surrounds the head 11).

The opening perimeters of the first and second corollas may be substantially equal (the second corolla likewise filtering the blood which passes through it).

In the unrestrained state of the retaining means, the extensions $15^1$ and $15_2$ run, in this case substantially over their all length, substantially parallel to the axis 2 and, in so doing, define a tubular surface having a cross-section substantially equal to that of the vessel, so that those extensions come into contact with the wall of the vessel and secure the filter there. Those extensions are directed towards the end $3^d$ of the filter, and thus the second corolla extends inside the tubular surface defined by the extensions.

In the case of temporary use of the filters $3_1$ and $3_2$, the extensions carrying the hooks 19 and also, in this case, the second legs are retained in the sleeve in a radially restrained state.

The extensions and the second legs may be constituted by round or flat metal wires, the second legs being, for example, soldered to the first corolla.

The filter $3_3$ of FIG. 11 is distinguished from that of FIG. 7 especially in that each second leg $13_3b$ and its extension $15_3$ are formed, preferably in one piece, by a flexible wire which is folded back on itself in loop(s) and the two opposing ends of which, positioned close to one another, are secured in the area of the head 11 (reference should be made to U.S. Pat. No. 5,344,427 for further details on the constitution of those legs $13_3b$ and their extensions). As regards at least some of the legs $13_3a$, they comprise a principal portion $131_3$ made of wire which is connected to the head and is extended by a distal portion $132_3$ having a contour which is non-aggressive with regard to the vessel and has a larger cross-section than that of the wire in order to increase the size of the support surface of the filter against the wall, reducing the likelihood of those distal portions being trapped by the tissues of the vessel.

In addition, the filters $3_3$ of FIG. 11 and $3_4$ of FIG. 10 are distinguished from the filters $3_1$ and $3_2$, respectively, in that the releasable connection means in this case comprise means for gripping or axially clamping the stem which are provided on the second legs $13_3b$ (filter $3_3$) and $13_4b$ (filter $3_4$) in an intermediate area $135_3$, $135_4$ between the head 11 and the proximal end of the filter (therefore at a distance from the opposing ends of the filter). Those gripping means cooperate with complementary means on the rod which comprise at least one cooperating abutment. In FIG. 11, the extensions $15_3$ are parallel to axis 2 only over part of their lengh.

In FIG. 13, the rod $9_3$ terminates in an enlarged end $9_3a$ which has two abutments $91_3$ and $92_3$, at least some of the legs $13_3b$ having locally a bent-back portion or crenel $30_3$ for accommodating that enlarged end. In the restrained state of the retaining means, when they are contained in the sleeve (temporary use of the filter), the crenels $30_3$ grip or trap the end $9_3a$ of the rod, being supported against the abutments in order to prevent any axial displacement of the rod relative to the filter. In the case of definitive use of the filter, the gripping means, outside the sleeve, are at a distance from the abutments as a result of the radial expansion of the second legs.

In FIGS. 10 and 12, at least some of the second legs $13_4b$ carry flexible tongues $30_4$ internally that protude from the legs in order to block the end $9_3a$ Those tongues extend, over the main part of their length, along the legs to which they are connected and move away therefrom towards one of their free ends to be supported, in $91_4$, the case of temporary use of the filter, when the legs $13_4b$ are restrained in the sleeve, against an enlarged tip profile $9_4a$ of the distal end of the rod, and a second abutment $92_4$ of that enlarged tip profile engages the head 11 of the filter at its top end $11a$ Thus, the tongues $30_4$, the head 11 of the filter and the enlargement $9_4a$ of the flexible rod are mutually engaged so that enlargement of the rod is clamped between the tongues and the filter head. In the unrestrained position of the legs $13_4b$, the tongues are moved away radially from the rod which is thus freed.

It can also be seen in FIGS. 10 to 13 that the rod has a small outside diameter ($D_4$) in relation to the inside diameter ($D_2$) of the sleeve, so that the second legs and their extensions are arranged between the rod and the sleeve when the filter is in the sleeve and in the case of temporary use of the filter.

Then, the flexible rod ($9_3$ or $9_4$) has at least an axial portion thereof (presently all its axial length except a terminal tip enlargement $9_3a$ or $9_4a$) having an external diameter $D_4$ (FIG. 12) smaller than the minimum diameter $D_5$ (FIG. 13) of an inherent internal passage 150 that the second legs $13_4b$ create therebetween when they are in their radially restrained state, as illusted in FIGS. 12 or 13.

Thus, said restricted diameter flexible rod is adapted to be inserted within the passage 150 and contained therein when the second legs are radially restrained in the sleeve.

Reference will now be made to FIGS. 4, 5 and 6 to describe a possible method of using the device 1 for the implantation of the filter 3.

For the general implanting technique, reference may be made especially to the above-mentioned publications or to patent U.S. Pat. No. 4,990,156, it being pointed out that, after having made an incision 27, an access route as far as the implanting area 51 of the filter is formed and then the introducing sleeve 5 is inserted so that it extends along the access route, its proximal end projecting from the body of the patient and its distal end being in the area 51. In this case, the positioning of the filter in a restrained state is then effected from the proximal end $5b$ of the sleeve, the filter 3 being pushed along that catheter by the rod 9 connected to the filter until it is positioned in the distal end of the sleeve (see FIG. 4).

In FIG. 5, as a result of a relative displacement of the sleeve in relation to the rod, the legs 13 of the filter and their extensions 15 are partially projecting from the sleeve. The filter is, of course, still connected to its maneuvering rod 9, the proximal end $9b$ of which still projects from the body of the patient so that it can be readily maneuvered by the practitioner.

FIG. 5 shows the device within the framework of a temporary filtration, the filter then being as in its position in FIG. 2 where the portion of its corolla disposed outside the sleeve opens out in such a manner that it occupies the main portion of the diameter of the vessel while performing its filtering role in respect of the blood flow schematized by the arrow 29. Of course, in that position the anchoring means 19 are always accommodated inside the sleeve, the portion of the extensions 15 still located inside the sleeve here being restrained along the legs, substantially in accordance with the same corolla configuration.

If, after a few days or weeks, the practitioner judges that the risk of embolism is sufficiently reduced, he can then withdraw the whole device, including the filter. In order to do that he has only to pull the sleeve towards the rear (arrow 33), therefore withdrawing the rod and the filter at the same time.

If, on the other hand, the practitioner realizes that a definitive implantation of the filter 3 is preferable, he has only to leave the sleeve 5 implanted and to act on the proximal end 9b of the rod 9 in order to unscrew it from the head of the filter, which is prevented from turning by the notches 25. At the same time, or immediately afterwards, he acts again on the sleeve by pulling it up relative to the rod 9, which is held secured in position, until all of the extensions 15 spread out laterally and the anchoring means 19 engage in the wall of the vessel, as shown in FIG. 6 which indicates that the means 15 define a substantially cylindrical tubular surface centered on the axis 33 of the vessel 31 against which they are applied, the filtering means 11, 13 extending inside that surface in order to retain any clots, while at the same time permitting the circulation of blood, the direction of flow of which is again schematized by the arrow 29.

Once the filter is thus positioned, the practitioner can of course withdraw the sleeve and the rod 9 (separated from the filter) via their implantation route, the filter being left where it is.

It is obvious that other variants of the invention could be envisaged. Thus, according to FIG. 9, the separable filter/rod connection could be ensured by at least one wire 100, or equivalent means, secured both to the rod 9, along which it extends, and to the filter (at its head 11) in order to keep them joined in the case of temporary use of the filter. The wire, for example made of stainless steel, is covered with an insulating coating (especially of Teflon) except in its portion 102 connecting the rod to the filter. In the case of definitive use of the filter, the wire may be destroyed locally or cut at the site of the joining portion 102, the practitioner acting from a distance. To that end, the proximal end of the wire is connected to a source of current arranged outside the body of the patient. The passage of current in the portion 102 which is in direct contact with the blood causes its electrolytic disintegration, thus bringing about the separation of the filter and the rod (reference should be made to U.S. Pat. No. 5,122,136 for further details). By way of variation and as detailed in U.S. Pat. No. 5,108,407, it would be possible to use an optical fiber (for example of quartz and covered with a silica coating) which extends along the rod, being connected at its distal end to a metal connector capable of being heated by light energy. That connector (which may consist of the distal end of the rod) is connected to the head of the filter by an adhesive substance capable of decomposing or of losing its adhesive properties at a specific temperature (which is a function of the substance and is selected to be greater than the body temperature of the patient). In order to separate the filter from the rod, radiation (preferably a laser beam) is emitted, via the optical fiber, as far as the connector which then heats and brings the adhesive to the temperature at which the filter becomes separated from the rod 9.

It would also be possible to use a mechanical "bayonet" connection or a biologically absorbable means which would become absorbed on contact with a specific biocompatible product.

As regards the filter, it could be the filter of application FR 92 09 845 (filter having triangulated legs) or that of application FR 92 15 774 with zig-zag-shaped extensions.

In order to position the filter, it would optionally be possible to use a supplementary catheter 35 in which the sleeve 5 could slide in order to facilitate its introduction into the vein and the operations for manoeuvring the device 1 (FIG. 5).

We claim:
1. A blood filter assembly comprising:
   a filter portion including:
   (a) a centrally located head;
   (b) first legs connected at first ends thereof to the centrally located head and diverging in a first direction to form a first conical profile when unrestrained;
   (c) second legs connected at first ends thereof to the centrally located head and diverging in a second direction, opposite the first direction, to form a second conical profile that is inverted with respect to the first conical profile, when unrestrained, the second legs defining an internal passage therebetween when restrained, said internal passage having a minimum diameter;
   an implantation portion including:
   (d) a sleeve for removably enclosing the filter portion in a radially restrained state;
   (e) a maneuvering flexible rod having a distal end and at least a portion of an external diameter smaller than said minimum diameter of the internal passage defined by the second legs in the radially restrained state, said at least a portion of the flexible rod being disposed in the passage between the second legs when the second legs are in the sleeve;
   (f) said distal end of the flexible rod and a profile of the head of the filter portion being engaged to complete a releasable connection between the flexible rod and the filter portion for displacing the filter portion from the sleeve into a blood vessel;
   (g) the connection existing when the filter portion is temporarily implanted in the vessel permitting axial displacement of the filter portion in axially opposite directions within the sleeve accompanied by retention of the second legs within the sleeve, and the connection being completely released during indefinite implantation of the filter portion in said vessel when the second legs are freed from the sleeve.

2. The assembly as set forth in claim 1, wherein the flexible rod is a catheter.

3. The assembly as set forth in claim 1, wherein:
   the filter portion further comprises first thread means formed on the head;
   the implantation portion further comprises second thread means formed on the distal end of the flexible rod, the first thread means engaging the second thread means to complete the connection between the flexible rod and the filter portion.

4. The assembly as set forth in claim 1, wherein the second legs of the filter portion are provided with securing means for engaging a wall of the vessel when the filter portion is indefinitely implanted in said vessel, whereas the first legs are free of such securing means.

5. The assembly as set forth in claim 1, further comprising a wire connected at one end of the flexible rod and, at the other end, to the head of the filter portion, said wire being adapted to rupture when subjected to a predetermined influence.

6. The assembly as set forth in claim 1, further comprising:

an optical fiber which extends along the flexible rod and which is connected, at a distal end, to a metal connector capable of being heated by light energy in order to separate the filter portion from the flexible rod;

the connector also being connected to the head of the filter portion by an adhesive substance capable of losing its adhesive properties at a specific temperature when the connector is heated by the optical fiber in order to release the filter portion for indefinite implantation of said filter portion in the vessel.

* * * * *